United States Patent [19]

Font Freide et al.

[11] Patent Number: 5,105,052

[45] Date of Patent: * Apr. 14, 1992

[54] PROCESS FOR THE PRODUCTION OF MONO-OLEFINS

[75] Inventors: Josephus J. H. M. Font Freide, Meybridge; Mark J. Howard, Twickenham; Trevor A. Lomas, Langley, all of England

[73] Assignee: British Petroleum Company p.l.c., London, England

[*] Notice: The portion of the term of this patent subsequent to Jul. 10, 2007 has been disclaimed.

[21] Appl. No.: 474,322

[22] Filed: Feb. 2, 1990

Related U.S. Application Data

[62] Division of Ser. No. 306,063, Feb. 6, 1989, Pat. No. 4,940,826.

[30] Foreign Application Priority Data

Mar. 8, 1988 [GB] United Kingdom ............... 8805447

[51] Int. Cl.$^5$ ............................................. C07C 4/06
[52] U.S. Cl. .................... 585/651; 585/652; 585/653; 585/661
[58] Field of Search ............... 585/654, 658, 81, 651, 585/652, 653, 661

[56] References Cited

U.S. PATENT DOCUMENTS

| | | | |
|---|---|---|---|
| 3,541,179 | 11/1970 | Okagami et al. | 260/683.3 |
| 3,562,797 | 10/1971 | Hu | 585/658 |
| 3,670,044 | 6/1972 | Drehman et al. | 260/683.3 |
| 3,793,225 | 2/1974 | Bertus et al. | 252/437 |
| 3,878,260 | 4/1975 | Kunugi et al. | 585/622 |
| 4,788,371 | 11/1988 | Imai et al. | 585/621 |
| 4,940,826 | 7/1990 | Font Freide et al. | |

FOREIGN PATENT DOCUMENTS

| | | |
|---|---|---|
| 178853 | 4/1986 | European Pat. Off. |
| 196758 | 10/1986 | European Pat. Off. |
| 323115 | 7/1989 | European Pat. Off. |
| 2203446A | 10/1988 | United Kingdom |

OTHER PUBLICATIONS

"Catalytic Oxidative Dehydrogenation ...", Journal of Catalysts 46, 424-425 (1977).

*Primary Examiner*—Anthony McFarlane
*Attorney, Agent, or Firm*—Nixon & Vanderhye

[57] ABSTRACT

Process for the production of a mono-olefin from a gaseous paraffinic hydrocarbon having at least two carbon atoms or a mixture thereof. The process includes the step of partially combusting, in contact with a combustion catalyst, the gaseous paraffinic hydrocarbon or a mixture of the gaseous paraffinic hydrocarbons and a molecular oxygen-containing gas in a composition of from 5 to 9 times the stoichiometric ratio of hydrocarbon to oxygen for complete combustion of carbon dioxide and water. In the process, the mixture is partially combusted at a temperature in the range of 500° to 1200° C. and at a gas hourly space velocity of at least 80,000 hr$^{-1}$.

14 Claims, No Drawings

PROCESS FOR THE PRODUCTION OF MONO-OLEFINS

This is a division of application Ser. No. 07/306,063, filed Feb. 6, 1989 now U.S. Pat. No. 4,940,826.

The present invention relates in general to the production of mono-olefins by the catalytic oxidative dehydrogenation of gaseous paraffinic hydrocarbons having 2 or more carbon atoms and in particular to the production of mono-olefins by the catalytic oxidative dehydrogenation of ethane, propane and butanes.

The prior art on the oxidative conversion of gaseous paraffins to mono-olefins can be broadly divided into two groups, depending on the temperatures employed. At low temperatures, typically below 500° C., oxidative dehydrogenation is generally a genuinely catalytic process. This is exemplified by U.S. Pat. No. 4,524,236 and EP-A-0189282. In the process of U.S. Pat. No. 4,524,236 ethane/oxygen mixtures are passed over catalysts comprising mixed oxides of molybdenum, vanadium, niobium and antimony (optionally incorporating a wide range of additional metals). Reaction takes place at temperatures in the range from 350° to 400° C. to give high selectivities to ethylene (i.e. 70% selectivity to ethylene at 75% ethane conversion). These catalysts produce only carbon oxides from higher paraffins. EP-A-0189282 discloses the use of a tin/phosphorus oxide catalyst in the production of mono-olefins from ethane, propane or butane in admixture with oxygen. Although reaction temperatures in the range 200° to 700° C. are disclosed, the working embodiment uses a temperature of only 550° C.

At higher temperatures, for example temperatures greater than 500° C., it is unlikely that reaction is entirely heterogeneous. At such temperatures thermal cracking and gas phase oxidations are likely to assume increasing importance. An example of prior art relevant to the high temperature reaction is U.S. Pat. No. 3,541,179 which discloses passing a paraffinic gas through an externally heated fluid bed of "fire resistant" particles containing from 0.5 to 20% wt of at least one of the metals copper, manganese or vanadium. An oxygen-containing gas is injected into the fluid bed. The reaction temperature is from 650° to 900° C. and the process is at least partially autothermal. At a molar ratio of $C_2H_6:O_2$ of 2.6:1 and about 840° C. about 90% of the ethane feed is converted to ethylene.

There are also a number of processes that do not involve catalysts at all. These are genuine high temperature autothermal cracking reactions and are exemplified by, for example, an article entitled "Autothermal Cracking for Ethylene Production" by R. M. Deanesly in *Petrol. Refiner*, 29 (September, 1950), 217 and GB-A-794,157.

A desirable objective would be to convert ethane, propane or butanes in a single step to mono-olefins.

Recently, the production of olefins together with carbon monoxide and hydrogen from gaseous paraffinic hydrocarbons, including ethane, by partial oxidation in spouted or fluid bed reactors has been disclosed in, for example, our copending applications EP-A-0164864 and EP-A-0178853.

The present invention provides a process for the production of a mono-olefin from a gaseous paraffinic hydrocarbon having at least two carbon atoms or a mixture thereof which process comprises partially combusting a mixture of the hydrocarbon(s) and a molecular oxygen-containing gas in contact with a catalyst capable of supporting combustion beyond the normal fuel rich limit of flammability.

As the gaseous paraffinic hydrocarbon there may suitably be used either ethane, propane or a butane, or a mixture of two or more thereof. A suitable feedstock hydrocarbon is a mixture of gaseous paraffinic hydrocarbons, principally comprising ethane resulting from the separation of methane from natural gas.

As the molecular oxygen-containing gas there may suitably be used either oxygen or air. It is preferred to use oxygen, optionally diluted with an inert gas, for example nitrogen. It is preferred to pre-mix the oxygen-containing gas and the paraffinic hydrocarbon prior to contact with the catalyst. Additionally, other feed components may be included if so desired to optimise process design. Examples of other suitable feed components include methane, hydrogen, carbon monoxide, carbon dioxide and water.

The preferred composition of the gaseous paraffinic hydrocarbon/molecular oxygen-containing gas mixture is from 5.0 to 9.0 times the stoichiometric ratio of hydrocarbon to oxygen for complete combustion to carbon dioxide and water, but these limits are extendible if desired. Typically, commercial reactors would be operated at pressures of approximately 1–5 bar above atmospheric.

A catalyst capable of supporting combustion beyond the normal fuel rich limit of flammability is employed. Suitable catalysts comprise supported platinum group metals and mixtures thereof, for example supported platinum or palladium. Although a range of support materials may be used, it is preferred to use an alumina as the support. The support material may be in the form of spheres or other granular shapes, but is preferably in the form of a monolith. Monoliths are continuous multi-channel ceramic structures, frequently of a honeycomb appearance. They are commercially available as similar materials are commonly used as catalytic convertors in automobile exhausts. A preferred form of alumina-supported platinum catalyst is platinum/gamma-alumina spheres. A more preferred form of supported platinum catalyst is a platinum/monolith, for example a platinum/cordierite or mullite monolith. Cordierite has a material composition of $2\ MgO.2Al_2O_3.5SiO_2$ whilst mullite has a material composition of $3Al_2O_3\ 2SiO_2$. The catalyst may suitably be prepared by impregnating the support with a solution of a soluble compound of the platinum group metal. Using a monolith catalyst, this may suitably be achieved by soaking the monolith in a solution of a soluble compound, for example a salt, of the metal, removing the monolith from the solution and drying, typically at about 120° C. Using the simple soaking method it is difficult to achieve high, i.e. greater than about 0.15% metal loadings. Although such a metal loading is adequate for the performance of the invention, in certain circumstances higher loadings may be desirable. A higher loading may be achieved by wash coating the monolith prior to immersion in the solution of the catalytic metal compound with a material, for example alumina, capable of facilitating the retention of the metal compound. A combustion catalyst in the form of a metallic gauze such as Pt/Rh may also be employed.

The catalyst in the form of spheres may be used as a solids recirculating bed, for example a fluid bed or a spouted bed.

A process for producing synthesis gas, i.e. carbon monoxide/hydrogen mixtures, from a reaction mixture comprising a saturated hydrocarbon and an oxygen-containing gas in a spouted bed, the bed comprising material which is catalytically active for steam reforming reactions, is described in our copending EP-A-0164864. The process described in EP-A-0164864, which is incorporated by reference herein, may be modified by the use of a catalyst capable of supporting combustion beyond the normal fuel rich limit of flammability, for example a supported platinum group metal(s) as hereinbefore described, instead of the steam reforming catalyst and the conditions modified in accordance with the process of the present invention to produce a monoolefin as the principal product of the process. In a preferred embodiment of the modified process of EP-A-0164864, hydrogen is co-fed to the process as described in our copending EP-A-0178853 which is also incorporated by reference herein.

It is preferred to use the catalyst in a fixed bed. One reason for this preference is that it largely avoids the attrition problems generally encountered in moving bed operations. In the context of fixed bed operation it is further preferred to use a monolith catalyst. Monolith catalysts are preferred over other forms of fixed bed catalyst because (1) they are capable of sustaining a very low pressure drop along the bed, thereby allowing large gas throughputs, (2) they present a high surface area to the gaseous combustion mixture, (3) they are particularly free from attrition problems, (4) they can result in very low levels of soot formation and as a result require less frequent de-coking and (5) they are available in various cell sizes and shapes and their preparation by the soaking technique is relatively simple.

The elevated temperature employed in the process of the invention may suitably be in the range from 500° to 1200° C., though temperatures in the upper part of this range, for example 800° to 1000° C. are preferred.

It is preferred but not essential to co-feed hydrogen gas. By so-doing the yields of and selectivities to desirable products can be improved. It is also preferred but not essential to preheat the feed gas, a suitable temperature being in the range 300° to 500° C.

In a preferred embodiment the present invention provides a process for the production of ethylene from ethane which process comprises contacting a mixture comprising ethane and oxygen in an ethane to oxygen molar ratio of 1.7 to 2.1 with a platinum- or palladium-containing monolith fixed bed catalyst.

In addition to ethylene, small amounts of higher olefins, acetylenes, aromatics and carbon oxides, i.e. carbon monoxide and carbon dioxide are co-produced.

The process of the invention will now be further illustrated by reference to the following Examples.

EXAMPLE A—PREPARATION OF PT/CORDIERITE MONOLITH

A cordierite monolith (ex CORNING) was soaked in a solution of $[(NH_3)_4Pt]Cl_2.H_2O$. After 2 weeks the Pt impregnated monolith was removed from the solution, allowed to drain and dried in air at 120° C. The platinum loading, as determined by X-ray Fluorescence Spectroscopy was about 0.1% w/w.

EXAMPLE 1

The Pt-loaded monolith (approximately 38 mm diameter × 51 mm length) was placed at the bottom of a quartz, 51 mm diameter, reactor with a baffle placed beneath it. The baffle ensured that the incoming flow of feed gas became evenly distributed through all cells in the monolith. Ethane, oxygen, hydrogen and nitrogen were preheat of the feed gases was required to effect autothermal operation, substantial heat generation being provided by the highly exothermic combustion of hydrogen/oxygen. Details of the molar proportions of the feed, the flow rates and the results obtained are given in Table 1.

TABLE 1

| Total Flow nl/min$^{-1}$ | $C_2H_6/O_2$ | $H_2/O_2$ | $N_2/O_2$ | Maximum Temperature (°C.) | Conversion (% mol) | Selectivity (% C mol) | | | | | | |
|---|---|---|---|---|---|---|---|---|---|---|---|---|
| | | | | | | $C_2H_4$ | $C_2H_2$ | $CH_4$ | CO | $CO_2$ | $C_3/C_4$ | $C_6H_6$ |
| 16.0 | 1.99 | 1.86 | 0.65 | 841 | 70.0 | 72.3 | 0.4 | 8.3 | 13.7 | 1.1 | 3.7 | 0.4 |
| 27.7 | 1.90 | 1.86 | 0.72 | — | 72.2 | 72.8 | 0.5 | 8.3 | 14.0 | 1.0 | 3.1 | 0.3 |
| 36.8 | 1.82 | 1.88 | 0.63 | 855 | 79.8 | 70.0 | 0.9 | 9.3 | 15.2 | 0.9 | 3.2 | 0.5 |

EXAMPLE 2

Into a 51 mm diameter quartz reactor was placed a catalyst in the form of previously calcined Pt/gamma-alumina spheres (2 mm diameter), supported on a coarse silica sintered disc.

Ethane, hydrogen, oxygen and nitrogen were passed over the catalyst in the molar proportions and under the conditions shown in Table 2. Also tabulated in Table 2 are the experimental results. No soot formation was observed.

EXAMPLE 3

In the following example, 0.5% Pt/Pd loaded alumina spheres (1.7 mm diameter) were placed into a quartz reactor (25 mm diameter). The catalyst was supported on a course silica sintered disc.

The appropriate paraffinic feedstock, ethane, propane or butane, or mixtures thereof, was co-fed with oxygen and nitrogen over the catalyst in the proportions and under the conditions shown in the following tables (3-4). Methane and hydrogen were also co-fed in some experiments.

The tables also show the experimental results, in which selectivities have been calculated on a soot free basis. Minimal soot formation was observed.

EXAMPLE 4

In the following example, the monolith or gauze was placed in a quartz reactor (25 mm diameter) and the catalyst was supported on a course silica disc.

Ethane, hydrogen, oxygen and nitrogen were co-fed over the catalyst in the molar proportions and under the conditions shown in the following tables (7-9).

Tables 7 to 9 also show experimental results in which selectivities have been calculated on a soot-free basis. No soot formation was observed.

TABLE 2

| Bed vol/cm³ | Total Flow nl/min⁻¹ | C₂H₆/O₂ | H₂/O₂ | N₂/O₂ | Maximum Temperature (°C.) | Conversion (% mol) | Selectivity (% C-mol) | | | | | | |
|---|---|---|---|---|---|---|---|---|---|---|---|---|---|
| | | | | | | | C₂H₄ | C₂H₂ | CH₄ | CO | CO₂ | C₃/C₄ | C₆H₆ |
| 12 | 27.8 | 1.75 | 2.45 | 0.76 | 887 | 72.1 | 62.6 | — | 4.3 | 29.0 | 2.1 | 1.9 | 0.2 |
| 12 | 37.4 | 1.78 | 2.47 | 0.56 | 916 | 79.1 | 66.3 | — | 5.7 | 23.4 | 1.5 | 2.1 | 0.1 |
| 12 | 55.3 | 1.90 | 1.99 | 0.57 | 922 | 80.4 | 68.9 | — | 6.4 | 19.8 | 1.4 | 2.6 | 0.1 |
| 25 | 27.3 | 1.76 | 2.38 | 0.75 | 933 | 74.9 | 64.8 | — | 4.3 | 26.9 | 2.0 | 1.2 | 0.1 |
| 25 | 37.0 | 1.78 | 2.45 | 0.54 | 980 | 81.4 | 68.8 | — | 5.7 | 20.5 | 1.3 | 2.3 | 0.1 |
| 25 | 55.0 | 1.89 | 1.96 | 0.55 | 983 | 82.2 | 71.2 | — | 5.9 | 17.3 | 1.2 | 3.0 | 0.2 |
| 55 | 27.7 | 1.75 | 2.43 | 0.74 | 933 | 69.1 | 58.4 | — | 3.5 | 33.6 | 3.2 | 1.3 | — |
| 55 | 37.8 | 1.78 | 2.47 | 0.65 | 977 | 77.3 | 67.8 | — | 4.7 | 23.0 | 1.8 | 2.0 | 0.1 |

TABLE 3

Autothermal cracking of propane over 0.5% Pt/Pd/Al₂O₃

| Example | GHSV (h⁻¹) | C₃H₈/O₂ | H₂/O₂ | N₂/O₂ | Conversion (% mol) | Selectivity (% C-mol) | | | | | | | | | | | |
|---|---|---|---|---|---|---|---|---|---|---|---|---|---|---|---|---|---|
| | | | | | | CO | CO₂ | CH₄ | C₂H₄ | C₂H₆ | C₂H₂ | C₃H₆ | other C₃ | C₄ | C₄⁻ | 1,3-C₄⁻ | C₅₊ |
| 3A | 235200 | 1.41 | | 0.48 | 87.3 | 17.4 | 3.9 | 16.7 | 40.6 | 3.2 | 0.9 | 14.1 | 0.2 | 0.1 | 2.0 | | 0.1 |
| 3B | 238800 | 1.65 | | 0.51 | 73.6 | 15.5 | 4.5 | 14.8 | 36.4 | 3.5 | 0.5 | 19.9 | 0.2 | 0.3 | 1.9 | | 2.2 | 0.3 |
| 3C | 256800 | 1.15 | 1.96 | 0.44 | 98.9 | 13.0 | 1.1 | 23.4 | 47.5 | 2.4 | 2.8 | 4.6 | 0.6 | — | 0.3 | 2.5 | 1.8 |
| 3D | 262800 | 1.29 | 3.23 | 0.54 | 88.8 | 7.2 | 0.8 | 21.8 | 47.0 | 3.4 | 0.9 | 13.3 | 0.4 | 0.3 | 1.1 | 1.8 | 2.0 |

TABLE 4

Autothermal cracking of iso-butane over 0.5% Pt/Pd/Al₂O₃

| Example | GHSV (h⁻¹) | iC₄/O₂ | H₂/O₂ | N₂/O₂ | Conversion (% mol) | Selectivity (% C-mol) | | | | | | | | | | | |
|---|---|---|---|---|---|---|---|---|---|---|---|---|---|---|---|---|---|
| | | | | | | CO | CO₂ | CH₄ | C₂H₄ | C₂H₆ | C₂H₂ | C₃H₈ | C₃C₆ | other C₃ | nC₄ | C₄⁻ | C₅₊ |
| 3E | 194400 | 1.06 | | 0.37 | 90.9 | 18.7 | 6.1 | 22.7 | 17.8 | 2.1 | 1.3 | 0.2 | 25.2 | 1.3 | — | 4.7 | — |
| 3F | 198000 | 1.32 | | 0.39 | 74.9 | 13.9 | 6.6 | 16.1 | 8.8 | 1.4 | 0.4 | 0.2 | 30.7 | 1.6 | — | 20.0 | 0.3 |
| 3G | 235200 | 1.04 | 2.13 | 0.44 | 94.2 | 11.8 | 2.0 | 28.3 | 24.3 | 2.0 | 1.8 | 0.2 | 17.2 | 1.0 | — | 10.7 | 0.7 |
| 3H | 264000 | 1.18 | 2.11 | 0.43 | 72.4 | 9.3 | 2.3 | 22.9 | 14.8 | 1.7 | 0.6 | 0.3 | 36.6 | 1.3 | 0.2 | 10.0 | — |

TABLE 5

Autothermal cracking of n-butane over 0.5% Pt/Pd/Al₂O₃

| Example | GHSV (h⁻¹) | nC₄/O₂ | H₂/O₂ | N₂/O₂ | Conversion (% mol) | Selectivity (% C-mol) | | | | | | | | | | | |
|---|---|---|---|---|---|---|---|---|---|---|---|---|---|---|---|---|---|
| | | | | | | CO | CO₂ | CH₄ | C₂H₄ | C₂H₆ | C₂H₂ | C₃H₈ | C₃C₆ | other C₃ | iC₄ | C₄⁻ | C₅₊ |
| 3I | 182400 | 1.00 | | 0.52 | 98.8 | 19.0 | 4.0 | 14.8 | 45.5 | 2.5 | 1.8 | 0.4 | 8.1 | 0.6 | — | 3.0 | 0.3 |
| 3J | 178800 | 1.16 | | 0.58 | 88.1 | 14.2 | 4.6 | 12.5 | 39.4 | 3.6 | 0.8 | 0.6 | 18.4 | 0.5 | tr | 5.0 | 0.4 |
| 3K | 260400 | 1.17 | 2.22 | 0.51 | 82.8 | 6.2 | 1.3 | 14.6 | 42.0 | 3.8 | 0.4 | 0.7 | 22.0 | 0.2 | 1.8 | 6.7 | 0.3 |
| 3L | 254400 | 1.45 | 2.24 | 0.54 | 63.6 | 4.4 | 1.2 | 13.8 | 36.2 | 4.1 | 0.2 | 0.8 | 30.5 | 0.2 | 0.7 | 7.4 | 0.5 |

TABLE 6

Autothermal cracking of mixed methane/ethane/propane feeds over 0.5% Pt/Pd/Al₂O₃

| Example | GHSV (h⁻¹) | CH₄/C₂H₆/C₃H₈/O₂ (% mol) | H₂/O₂ | Feed hydrocarbon composition (% wt) | | | CONVERSION (% mol) | | Selectivity (% C-mol) | | | | | | | | |
|---|---|---|---|---|---|---|---|---|---|---|---|---|---|---|---|---|---|
| | | | | CH₄ | C₂H₆ | C₃H₈ | C₂H₆ | C₃H₈ | CO | CO₂ | CH₄ | C₂H₄ | C₂H₂ | C₃H₆ | other C₃ | C₄⁻ | C₅₊ |
| 3M | 388400 | 1.80 | | 17.6 | 32.8 | 49.6 | 93.2 | 99.9 | 30.8 | 4.1 | 13.6 | 45.6 | 5.2 | — | 0.2 | 0.5 | — |
| 3N | 340800 | 2.12 | | 17.4 | 32.4 | 50.2 | 74.4 | 96.1 | 24.4 | 4.4 | 12.7 | 53.3 | 1.5 | 1.6 | 0.3 | 1.8 | — |
| 3P | 344400 | 2.45 | | 17.2 | 32.2 | 50.6 | 54.4 | 84.4 | 21.3 | 5.5 | 11.1 | 51.7 | 0.7 | 6.4 | 0.4 | 2.7 | 0.2 |
| 3Q | 358800 | 1.98 | 1.67 | 18.1 | 33.3 | 48.6 | 85.5 | 99.3 | 19.3 | 1.3 | 17.4 | 58.5 | 1.6 | — | 0.2 | 1.4 | 0.3 |
| 3R | 357600 | 2.46 | 1.65 | 17.8 | 33.0 | 49.2 | 61.5 | 91.1 | 12.6 | 1.3 | 14.9 | 62.1 | 1.6 | 4.5 | 0.1 | 2.5 | 0.4 |
| 3S | 352800 | 2.79 | 1.69 | 17.6 | 33.1 | 49.4 | 43.4 | 75.2 | 10.4 | 1.3 | 13.5 | 59.6 | 0.4 | 10.9 | 0.3 | 3.0 | 0.6 |

TABLE 7

Autothermal cracking of ethane over a Pt/Rh gauze

| Example | Total Flow (l/min) | C₂H₆/O₂ | H₂/O₂ | N₂/O₂ | Conversion (% mol) | % C-mol Selectivity | | | | | | | |
|---|---|---|---|---|---|---|---|---|---|---|---|---|---|
| | | | | | | CO | CO₂ | CH₄ | C₂H₄ | C₂H₂ | C₃'s | C₄'s | C₅₊ |
| 4A | 16.9 | 1.79 | — | 0.29 | 94.7 | 26.8 | 3.3 | 10.2 | 51.9 | 3.6 | 1.0 | 2.2 | 1.0 |
| 4B | 16.8 | 1.98 | — | 0.31 | 88.3 | 23.4 | 3.6 | 8.7 | 58.0 | 1.5 | 1.5 | 2.2 | 1.9 |
| 4C | 22.9 | 1.83 | 2.16 | 0.32 | 89.5 | 19.3 | 1.0 | 10.4 | 63.2 | 2.1 | 0.9 | 1.6 | 1.5 |
| 4D | 22.3 | 1.83 | 1.74 | 0.32 | 91.1 | 19.4 | 1.0 | 10.5 | 60.8 | 2.3 | 1.1 | 2.1 | 2.8 |

TABLE 8

Autothermal cracking of ethane over a Pt/Pd loaded MULLITE monolith

| Example | GHSV | $C_2H_6/O_2$ | $H_2/O_2$ | $N_2/O_2$ | Conversion (% mol) | % C-mol Selectivity ||||||||
|---|---|---|---|---|---|---|---|---|---|---|---|---|---|
| | | | | | | CO | $CO_2$ | $CH_4$ | $C_2H_4$ | $C_2H_2$ | $C_3$'s | $C_4$'s | $C_{5+}$ |
| 4E | 144286 | 1.73 | 0.64 | 0.34 | 95.8 | 21.7 | 1.5 | 9.7 | 57.5 | 4.7 | 0.7 | 2.9 | 1.4 |
| 4F | 164429 | 1.90 | 1.67 | 0.38 | 89.6 | 16.6 | 0.7 | 9.3 | 67.4 | 2.1 | 0.9 | 2.5 | 0.5 |

TABLE 9

Autothermal cracking of ethane over Lithum Aluminium Silicate (LAS) monolith
(feed pre-heated to 300° C.)

| Example | GHSV | $C_2H_6/O_2$ | $H_2/O_2$ | $N_2/O_2$ | Conversion (% mol) | % C-mol Selectivity ||||||||
|---|---|---|---|---|---|---|---|---|---|---|---|---|---|
| | | | | | | CO | $CO_2$ | $CH_4$ | $C_2H_4$ | $C_2H_2$ | $C_3$'s | $C_4$'s | $C_{5+}$ |
| 4G | 80124 | 1.91 | — | 0.41 | 94.7 | 27.7 | 2.4 | 12.3 | 49.5 | 3.7 | 0.7 | 2.2 | 1.5 |
| 4H | 80071 | 2.09 | — | 0.42 | 89.9 | 24.4 | 2.5 | 10.9 | 56.4 | 1.9 | 0.9 | 2.1 | 0.9 |
| 4I | 118407 | 1.83 | 1.75 | 0.38 | 96.2 | 23.0 | 1.0 | 13.3 | 52.6 | 5.6 | 0.5 | 2.4 | 1.6 |
| 4J | 128018 | 2.24 | 1.98 | 0.45 | 85.2 | 16.5 | 0.8 | 10.1 | 67.5 | 1.4 | 0.9 | 2.1 | 0.7 |

We claim:

1. A process for the production of a mono-olefin from a gaseous paraffinic hydrocarbon having at least two carbon atoms or a mixture thereof, which process comprises the step of partially combusting
said gaseous paraffinic hydrocarbon or a mixture of said gaseous paraffinic hydrocarbons and a molecular oxygen-containing gas in a composition of from 5 to 9 times the stoichiometric ratio of hydrocarbon to oxygen for complete combustion of carbon dioxide and water, in contact with a combustion catalyst and in which process the mixture is partially combusted at a temperature in the range from 500° to 1200° C. and at a gas hourly space velocity (GHSV) of at least 80,000 $hr^{-1}$.

2. A process according to claim 1, wherein the catalyst is a supported platinum group metal or a mixture thereof.

3. A process according to claim 1, wherein the platinum group metal is either platinum or palladium.

4. A process according to claim 2, wherein the support is an alumina.

5. A process according to claim 2, wherein the support is a monolith.

6. A process according to claim 2, wherein the catalyst is platinum/gamma-alumina spheres.

7. A process according to claim 2, wherein the catalyst is platinum/cordierite monolith.

8. A process according to claim 5, wherein the catalyst is platinum/mullite monolith.

9. A process according to claim 2, wherein the catalyst is a metallic gauze containing a platinum group metal.

10. A process according to claim 1, wherein the gaseous paraffinic hydrocarbon is ethane, propane, butane or a mixture thereof.

11. A process according to claim 10, wherein the molecular oxygen-containing gas is oxygen.

12. A process according to claim 1, wherein hydrogen is co-fed.

13. A process according to claim 1, wherein the catalyst is in the form of a fixed bed.

14. A process according to claim 1, wherein the temperature is in the range from 800° to 1000° C.

* * * * *